United States Patent [19]

Yamaguchi et al.

[11] Patent Number: 5,550,026
[45] Date of Patent: Aug. 27, 1996

[54] ANTIBODIES TO HUMAN GASTRIN-RELEASING PEPTIDE PRECURSOR AND USE THEREOF

[75] Inventors: Ken Yamaguchi, c/o National Cancer Center Research Institute 1-1, Tsukiji 5-chome, Chuo-Ku, Tokyo; Yoshio Miyake, Tokyo, both of Japan

[73] Assignees: Tonen Corporation; Terumo Corporation; Ken Yamguchi, Tokyo, Japan

[21] Appl. No.: 15,180

[22] Filed: Feb. 11, 1993

[30] Foreign Application Priority Data

Jun. 12, 1992 [JP] Japan ..................... 4-153643

[51] Int. Cl.⁶ .............. G01N 33/53; C12N 5/12; C07K 16/26
[52] U.S. Cl. .......... 435/7.1; 435/7.92; 435/240.27; 530/387.7; 530/387.9; 530/388.24; 530/388.8; 530/388.85; 530/389.2; 530/389.7
[58] Field of Search ............ 530/387.1, 387.7, 530/387.9, 388.24, 388.8, 388.85, 389.2, 389.7; 435/240.27, 7.1, 7.92

[56] References Cited

PUBLICATIONS

M. E. Sunday et al., B10515 Abstract No. 92:50892, Hum. Pathol. 22(10), pp. 1030–1039, 1991.
E. Bork et al., B10515 Abstract No. 88:377073, Eur. J. Cancer Clin. Oncol. 24(6), pp. 1033–1038, 1988.
J. J. Holst et al., B10515 Abstract No. 90:90699, J. Clin. Oncol. 7(12), pp. 1831–1838, 1989.
K. Maruno et al., B10515 Abstract No. 89:138029, Cancer Res. 49(3), pp. 629–632, 1989.
Sunday et al., Human Pathology, vol. 22, No. 10, pp. 1030–1039 (1991).
Sunday et al., 45th Annual National Meeting of the American Federation for Clinical Research, Washington D.C., Apr. 29–May 2, 1988, Clinical Research, vol. 36(3) p. 500A 1988.
T. Goodman, Basic & Clinical Immunology, Fudenberg et al. (ed.), Lange Medical Publications, Los Altos, pp. 32–40, 1976.
Köhler et al., Nature, vol. 256, pp. 495–497 (1975).
Holst et al., Journal of Clinical Oncology, vol. 7, No. 12, pp. 1831–1838, (1989).
W. Cuttitta et al., Journal of Clinical Endocrinology and Metabolism, vol. 67, No. 3, pp. 576–583 (1988).
US News & World Report, p. 61, Aug. 15, 1994.

*Primary Examiner*—Christina Y. Chan
*Attorney, Agent, or Firm*—Foley & Lardner

[57] ABSTRACT

Antibodies made to a flanking region GPR(31-8) in human gastrin-releasing peptide (GRP) precursor. Since the antibodies have high affinity to GRP precursor, and the GPR precursor is highly stable in the blood, then lung cancer, especially small cell lung cancer can be diagnosed with high reliability by detecting or measuring GRP precursor in the blood of a patient using the present antibodies.

3 Claims, 6 Drawing Sheets

FIG. 1

```
              H1
   AATTC ATG AGT ACT GGT GAG AGC TCT
       G TAC TCA TGA CCA CTC TCG AGA
                  L1

TCT GTT TCT GAA CGT GGA TCC |CTT AAG
   AGA CAA AGA CTT GCA CCT AGG  GAA TTC|

H2
   CAG CAG CTT CGC GAA TAC ATC CGT TGG
   GTC GTC GAA GCG CTT ATG TAG GCA ACC
                  L2

GAA GAA GCT GCT CGT AAC CTG |CTA GGC
   CTT CTT CGA CGA GCA TTG GAC  GAT CCG|

H3
   CTG ATC GAA GCT AAA GAA AAC CGT AAC
   GAC TAG CTT CGA TTT CTT TTG GCA TTG
                  L3

CAC CAG CCG CCG CAG CCG AAA |GCT TTA
   GTG GTC GGC GGC GTC GGC TTT  CGA AAT|

H4
   GGT AAC CAG CAG CCG TCT TGG GAC TCT
   CCA TTG GTC GTC GGC AGA ACC CTG AGA
                  L4

GAA GAC TCT TCG AAC TTT AAA GAC TAA TAA
   CTT CTG AGA AGC TTG AAA TTT CTG ATT ATT
```

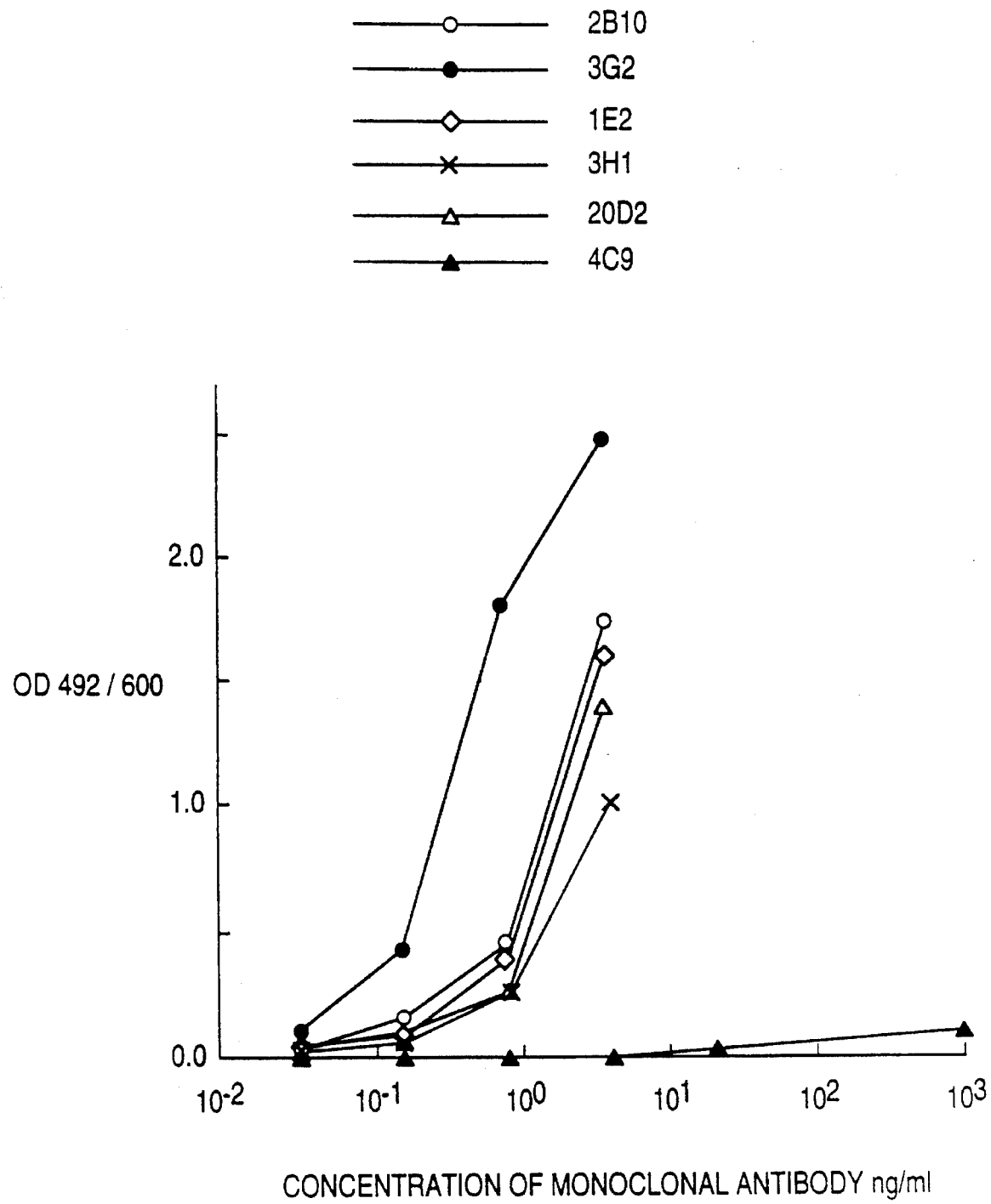

ANTIBODIES TO HUMAN GASTRIN-RELEASING PEPTIDE PRECURSOR AND USE THEREOF

BACKGROUND OF THE INVENTION

1. Field of the Invention

The present invention relates to antibodies to human gastrin-releasing peptide (GRP) precursor, and the use of the antibodies as a diagnostic agent for cancer.

2. Related Art

It is known that cancer cells produce substances specific to the cancer cells as well as substances common between normal cells and cancer cells. It has become possible to diagnose the characteristics of cancer cells and patients with cancer by measuring the cancer-specific substance. Substances specifically produced by cancer cells include oncogene products and growth factors, which are responsible for oncogenesis, growth and developments of cells. Moreover, it is considered that the production of carcinoembryotic proteins, hormones and enzymes and the like are characteristics of the oncogenesis. Therefore, if one of substances which define cancer cells, i.e., so-called tumor markers can be assayed with high sensitivity, diagnosis of cancers becomes possible.

Since the presence of neuroendocrine particles in small cell lung cancer was observed in 1968, it has been asserted that small cell lung cancer is derived from neuroendocrine cells, and at present, is included in APUD (amine precursor uptake and decarboxylation)-type tumors, and is distinguished from other non-small cell lung cancers which are epithelial tumors. It has been known that the small cell lung cancer shows the characteristics of the neuroendocrine cells in a cytobiological study, and is reported to produce peptide hormones such as serotonin, adrenocorticotropic hormone (ACTH), calcitonin, gastrin releasing peptide (GRP) etc., to exhibit high L-dopa decarboxylase (L-DDC) activity characteristic to APUD-type cells or tumors, and to exhibit high activities of neuron specific enolase (NSE) and creatine kinase BB (CK-BB), which are specific to neuron cells.

Analysis of a surface antigen of small cell lung cancer based on various biological properties of the cells as indicators using a monoclonal antibody was started with a report by Minna, Science 214, 1246–1248, 1981, and has been well developed by a lot of researchers. Assay systems so far practically used as tumor markers include those using carcinoembryonic antigens such as carcinoembryonic antigen (CEA), α-fetoprotein (AFP), Carbohydrate Antigen 125 (CA125); enzymes such as NSE, L-DDC, CK-BB; hormone-related substances such as ACHT, alcohol dehydrogenase (ADH). However, the positive ratio for sera of patients with cancer obtained using the above assay systems is at most 50 to 60%, while frequently patients having cancer provide negative result.

So far, GRP is known as one of tumor markers of small cell lung cancer. GRP is a peptide consisting of 27 amino acids extracted from the stomach of porcine by McDonald in 1978, and has activities to stimulate secretion of gastric acid, various hormones etc. There are three precursor proteins different in their C-terminal structure due to alternative splicing of RNA. Recently, the production of GRP as an autocrine growth factor in small cell lung cancer was found, and it is interested as a tumor marker.

In patients with small cell lung cancer, about 80% of the cases provide increased blood GRP concentration. Moreover, even in the cases of early phase, the blood GRP concentration is in an increased level, and therefore it is promised that a diagnostic of cancer using GRP as a marker is highly effective. However, conventional assay methods for GRP use antibodies to an active peptide, GRP(1-27), and its sensitivity is too low to be practically used. It is supposed that one of main reasons of difficulty to measure a serum GRP concentration using an antibody to GRP(1-27) is instability of GRP(1-27) in the blood.

Holst et al. (J. Clin. Oncol. 7, 1831–1838, (1989)) developed a radioimmunoassay (RIA) system using polyclonal antibodies to a synthetic peptide corresponding to the portion from 42 to 53 positions of C-terminal flanking peptide of GRP precursor, and demonstrated that GRP precursor protein can be a powerful diagnostic marker for small cell lung cancer. However said system was not practical because it provided an insufficient positive ratio due to its sensitivity. Because the antigen protein used was a part of GRP precursor, resulting antibody had low sensitivity and specificity body. Moreover, the low sensitivity of the assay system needed an extraction of the analyte protein from a large amount of a sample, resulting in difficulty in clinical application of the system. GRP precursor protein present in the blood is a macromolecule having a molecular weight of 8,000 to 100,000. Therefor, in an assay system using antibodies to GRP(42-53) which is a part of GRP precursor, sensitivity and specificity are limited.

In normal cells, a protein is produced in the rough-surfaced endoplasmic reticulum, concentrated in the Golgi apparatus resulting in formation of secretory granules in which the protein is packed, and extracellularly secreted through so-called regulated pathway. Since the secretory granules contain proteolytic enzymes, a precursor of the protein can be adequately processed during passing through the regulated pathway. On the other hand, in cancer cells, since the rough-surfaced endoplasmic reticulum is remarkably developed while the number of the secretory granules is small, then when GRP is produced and secreted, GRP precursor is extracellularly secreted through the constitutive pathway from the rough-surfaced endoplasmic reticulum without being affected by action of any proteolytic enzymes, rather than passing through the regulated pathway involving the secretory particles. Therefore, the blood of patients with cancer contains precursor GRP and flanking peptides in addition to an active peptide GRP (1-27).

Compared with GRP(1-27), the active site-free flanking peptide of GRP precursor is expected to be stably present at a high concentration in the blood.

SUMMARY OF THE INVENTION

Accordingly, the present invention provides novel antibodies to a region so far not used as an antigen in a GRP precursor and capable of diagnosis of lung cancers with a high sensitivity, and a lung cancer diagnostic agent comprising the antibody.

In accordance with the present invention, novel antibodies are provided using a peptide having an amino acid sequence from the 31st Ser to the 98th Asp of GRP precursors as an antigen. The peptide contains common sequence among 3 GRP precursors but not a GRP active site in GRP precursors. The antibodies have a high affinity specificity to GRP precursors and therefore are useful for diagnosis of lung cancers.

More specifically, the present invention provides an antibody to a peptide having the amino acid sequence shown in SEQ. ID NO: 1, and reactive with human GRP precursors.

The present invention further provides a monoclonal antibody to human GRP precursor having a dissociation constant Kd of $3 \times 10^{-8} - 5 \times 10^{-7}$M for immunocomplex formed from the monoclonal antibody and the human GRP precursor.

The present invention further provides a lung cancer diagnostic agent comprising said antibody and a carrier.

The present invention still more provides hybridomas producing said monoclonal antibody.

The present invention further provides a process for production of a human GRP precursor antigen, comprising culturing a host transformed with an expression vector comprising a coding region coding for the amino acid sequence shown in SEQ ID NO: 1, and recovering the human GRP precursor antigen from the culture. Note, "pro-GRP" means precursor of GRP.

BRIEF EXPLANATION OF DRAWINGS

FIG. 1 represents a nucleotide sequence of DNA coding for proGRP(31-98) and of oligonucleotides for synthesizing the DNA.

FIG. 2 represents an example of measurement of GRP precursor in sera from patients with small cell lung cancer, using anti-GRR (31-98) antibodies of the present invention.

FIG. 4A shows the stability of GRP 1-27 and FIG. 4B shows the stability of GRP(31-98).

FIG. 5 is a graph showing affinity to proGRP of various monoclonal antibodies of the present invention.

Figure 2:
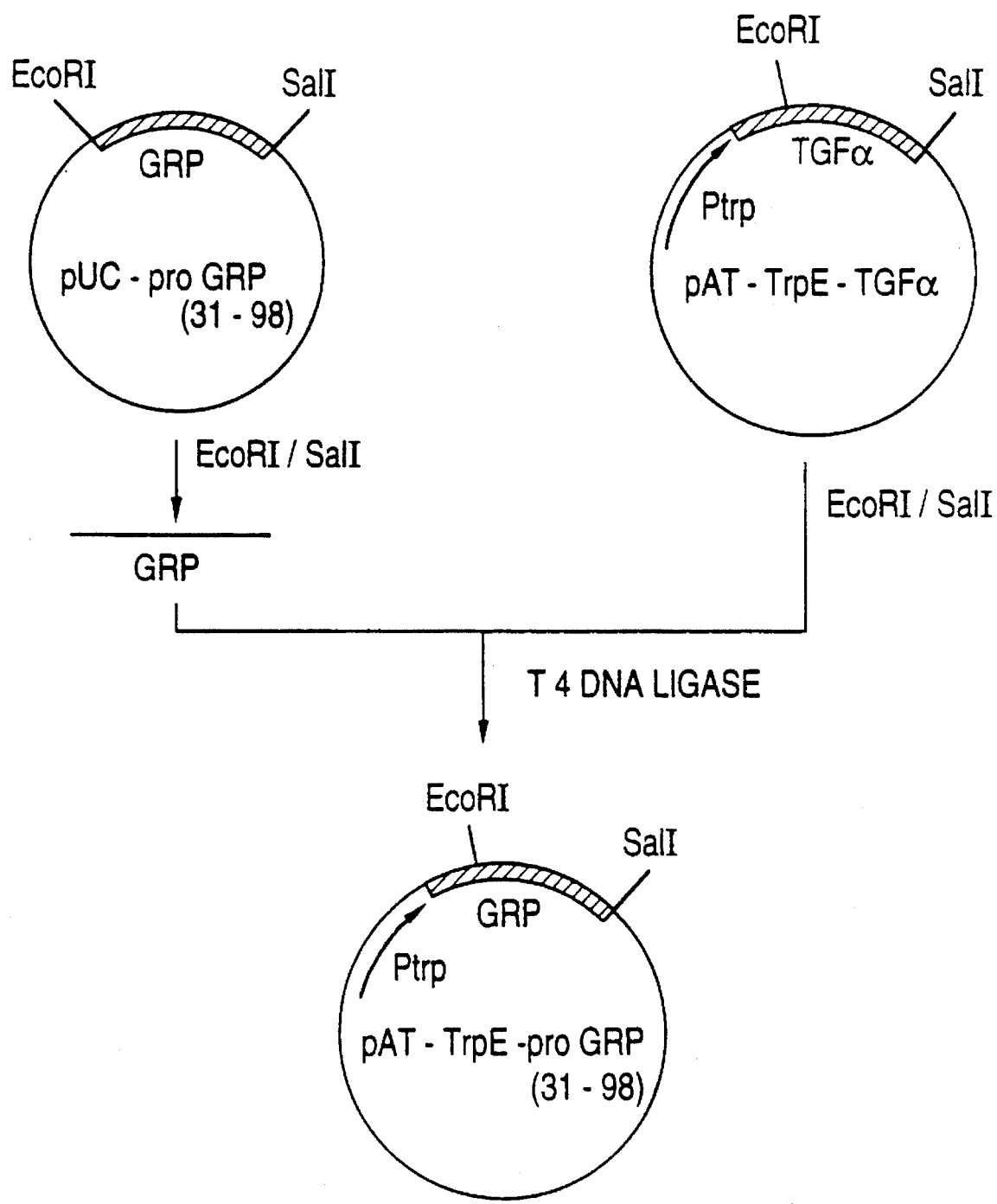
FIG. 2 represents a process for the construction of an expression plasmid pAT-TrpE-proGRP(31-98) for the production of proGRP(31-98).

PREFERRED EMBODIMENT FOR CARRYING-OUT THE INVENTION (1) Antigen protein and process for preparation thereof In a process for in vivo production of GRP, three GRP mRNAs are generated by alternative splicing of a mRNA, and three precursor proteins having a common amino acid sequence up to the 98 position including the active site but having different C-terminal structures are formed. The GRP precursor antigen used in the present invention is a peptide having an amino acid sequence from the 31th Ser to 98th Asp of the precursor protein, which is common between three GRP precursors and protein, which is common between three GRP precursors and does not contain GRP active region. The number of amino acids used in the present invention is determined by taking the N-terminal amino acid val of mature GRP as the first position. Therefore, the mature GRP is represented by GRP(1-27), and the present antigen peptide is represented by proGRP(31-98).

An amino acid sequence of the present GRP precursor antigen proGRP(31-98) and an example of nucleotide sequences coding therefor are shown in SEQ ID NO: 1.

The antigen peptide of the present invention can be prepared by chemical synthesis or genetic engineering. Since the chemical synthesis of peptides having more than 40 amino acids is difficult, genetic engineering is preferable.

The production of the present antigen peptide by genetic engineering can be carried out by transforming a host such as *E. coli* with an expression vector capable of expressing the present antigen peptide in the host such as *E. coli*, culturing the transformant, and recovering the antigen peptide from the cultured bacterial cells.

Although the above-mentioned expression vector may contain any nucleotide sequence coding for the present antigen polypeptide, in the case of an *E. coli* host, a nucleotide sequence comprising codons frequently used in *E. coli* and not containing palindrome is preferable.

As a nucleotide sequence coding for the amino acid sequence of proGRP(31-98), the nucleotide sequence shown in SEQ ID NO: 1 is preferable.

A promoter such as a tryptophan promoter is present upstream of the coding region for the present peptide to enhance transcription efficiency in a host used such as *E. coli*. Although the peptide coding region may be present immediately downstream of the promoter, the coding region may be present downstream of a coding region for a protein inherently produced by a host such as *E. coli* Trp E protein, as described hereinafter. In the latter case, the present peptide may be obtained as a fusion protein.

An expression vector of the present invention, as with conventional expression vectors, contains a selective marker such as antibiotic resistance and an origin of replication for replicating in a host such as *E. coli*. Moreover, a translational stop codon is positioned downstream of the peptide coding region. As a starting material for the construction of the expression vector, for example, pUC9, pBR322, and other vector such as commercially available vectors may be used.

The above-mentioned expression vector may be constructed by synthesizing the present peptide coding region by a known synthetic process such as phosphoramidite method, and cloning it into a vector such as a known vector expressed in a host such as *E. coli* host. In Examples described hereinafter, the GRP coding region was inserted into TrpE gene or TGF-α gene (see Japanese Patent Application No. 63-28908) present downstream of *E. coli* tryptophan promoter.

Transformation with an expression vector can be carried out according to a conventional procedure. Culturing conditions of host such as *E. coli* is also conventional.

The present peptide produced by a host such as *E. coli* transformed with a vector can be isolated and purified by, for example, collecting cells by, for example, centrifugation, disrupting the cells by well known lysozyme treatment and/or ultrasonication, and applying the disruptant to a gel filtration chromatography or the like. Definite conditions for isolation and purification of the peptide is described hereinafter in Examples.

(2) Production of antibody

Mouse such as Balb/C mouse is periodically immunized by peritoneal or subcutaneous administration of the present antigen alone or as an antigen prepared by binding the present antigen with a hapten such as bovine serum albumin (BSA), keyhole limpet hemocyanin (KLH) etc., in a mixture with Freund's complete adjuvant. After antibody titer in the blood is increased, the mouse is boosted by administrating the present antibody through a tail venous of mouse. After that, the spleen is removed and spleen cells are fused with appropriate myeloid cells such as mouse myeloid cells. This procedure can be carried out according to Kohler and Milstein, Nature 256, p495–497, 1975, to obtain hybridomas.

The hybridomas thus obtained are cultured in an appropriate medium, and a hybridoma cell line producing an antibody specifically reactive with the present antigen is selected and cloned. Next, monoclonal antibody produced is recovered by, for example, column chromatography.

Polyclonal antibodies can be prepared by periodically immunizing an animal such as a guinea-pig, rabbit, goat, sheep, etc., with the present antigen alone, or in a form of conjugate with bovine serum albumin (BSA) or keyhole limpet hemocyanin (KLH) etc. by means of a foot pad, intramuscular injection or subcutaneous injection, as a mixture with Freund's complete adjuvant. An increase of antibody titer in the blood is tested, the whole blood is obtained and polyclonal antibody is recovered by column chromatography or the like.

Monoclonal antibody or polyclonal antibody thus obtained can be used to carry out ELISA or other immunoassays such as IRMA, RIA, FIA, CIA, etc. to measure GRP precursor for example in a blood sample.

EXAMPLES

The present invention will now be further illustrated by, but not limited to, the following examples.

Example 1

Preparation of proGRP(31-98)

(1) Construction of cloning vector

As shown in FIG. 1, GRP gene is divided into DNA fragments of about 60 bases, and each DNA fragment was synthesized by phosphoramidits method.

| Fragment | SEQ ID NO | Fragment | SEQ ID NO |
|---|---|---|---|
| H1 | 3 | L1 | 7 |
| H2 | 4 | L2 | 8 |
| H3 | 5 | L3 | 9 |
| H4 | 6 | L4 | 10 |

The synthesized DNA fragments were purified by reversed phase chromatography and ligated by T4 DNA ligase to obtain the GRP gene.

The gene thus obtained having a restriction enzyme EcoRI site and SalI site at the 5'- and 3'-termini respectively was inserted into an EcoRI/SalI-digested cloning vector pUC9. The ligation product was used to transform *E. coli* JM107, which was then cultured overnight in L medium in the presence of 40 µg/ml ampicillin, isopropyl thiogalactoside (IPTG) and X-gel to obtain a candidate strain.

Plasmid was extracted from the candidate strain, and the nucleotide sequence of the inserted gene was tested by Sanger method to confirm that the inserted gene has an expected nucleotide sequence. *E. coli* containing a cloning vector comprising a desired GRP gene was designated as pUC-proGRP(31-98)/JM107, and the cloning vector was designated as pUC-proGRP(31-98).

(2) Construction of expression vector (FIG. 2)

The vector pUC-proGRP(31-98) was digested with EcoRI and SalI, and a GRP gene fragment of about 220 base pairs was extracted. On the other hand, an expression vector pAT-TrpE-TGF-α was digested with restriction enzymes EcoRI and SalI to obtain a larger fragment, which was then ligated with the GPR gene fragment using T4 DNA ligase. The ligation product was used to transform *E. coli* HB101, which was then cultured overnight in L medium in the presence of 40 µg/ml ampicillin to obtain a candidate strain. The candidate strain was designated as pAT-TrpE-DROGRP(31-98)/HB101, and the expresstion vector thus obtained was designated as pAT-TrpE-DROGRP(31-98).

(3) Purification of expressed polypeptide

The above-constructed strain containing the expression vector, pAT-TrpE-DROGRP(31-98)/HB101 was cultured and the expression of recombinant protein was tested. Namely, the strain pAT-TrpE-DROGRP(31-98)/HB101 was cultured overnight in 32 ml of LB medium containing 40 µg/ml ampicillin, and the resulting culture was inoculated to 3.2L of M9 medium containing 0.5% casamino acid and culturing was carried out at 37° C. When the absorbance at 600 nm reached 0.4, indolacrylic acid (IAA) was added to the culture to a final concentration of 30 µg/ml, and culturing was further continued for 20 hours. The culture was centrifuged to collect 10 g of cells. The collected cells were suspended in a 100 mM Tris-HCl (pH 8.0) buffer containing 2 mg/ml lysozyme and 2 mM EDTA, and the suspension was allowed to stand at 0° C. for 30 minutes. The suspension was further ultrasonicated and centrifuged to obtain an insoluble fraction as a precipitate.

The insoluble fraction thus obtained was solubilized by the addition of 8M urea, and centrifuged to collect a supernatant. The supernatant was subjected to a column chromatography using DEAE TOYOPEAL (TOSO Co.) (eluate: A=20 mM Tris-HCl/6M urea (pH 8.0); B=0.5M NaCl/eluate A (pH 8.0); concentration gradient: from A to B with linear gradient/300 minutes; column ϕ1.6×40 cm; flow rate 1 ml/min.) to isolate and purify the desired protein. The eluted fractions were gathered, dialysed and lyophilized. The protein was cleaved with cyanogen bromide to remove TrpE moiety. The cyanogen bromide cleavage was carried out by adding the protein to a 70% formic acid solution to a protein concentration of 1%, adding 100 equivalent amount of cyanogen bromide thereon, and the resulting reaction mixture was allowed to stand at 37° C. for 24 hours. The mixture was dialysed, lyophilized and subjected to reversed phase high performance liquid chromatography (eluate: A=0.1% trifluoroacetic acid/water, B=60% acetonitryle/0.1% trifluoroacetic acid/water) to purify and obtain 30 mg of GRP protein. Purity of the protein was homogeneous as determined by reversed phase column chromatography and SDS-polyacrylamide gel electrophoresis. Moreover, it was confirmed that the protein has an amino acid sequence of GRP as determined by a peptide sequencer.

Example 2

Production of polyclonal antibody

The product DROGRP(31-98) thus prepared was conjugated with KLH as carrier protein, and 150 µg of the conjugate was first injected to a rabbit NZW, and a further 100 µg injected after two weeks, 100 µg after 2 weeks, 85 µg after 6 days, 80 µg after 12 days and 60 µg after 12 days were injected. After an increase of antibody titer was confirmed, the whole blood was obtained.

Example 3

Production of monoclonal antibody

DROGRP(31-98) was conjugated with KLH as carrier protein, and the conjugate was first injected to a Balb/c mouse, and a further injected 50 µg after 3 weeks, 50 µg after three weeks, 50 µg after 4 weeks and 30 µg after 4 weeks were injected.

Spleen cells ($1 \times 10^8$ cells/ml) from the immunized mouse were mixed with previously cultured myeloma cells P3U1 ($1 \times 10^7$ cells/ml) at a mixing ratio of 10:1 by cell amount, and the mixture was incubated at 37° C. for 5 minutes.

Next, to the mixture was added 50% polyethylene glycol 1500 followed by RPMI 1640 medium. After centrifugation, HAT medium containing 20% FCS was added thereon, and after adjusting cell concentration to $10^5$ cells/ml, the cell suspension was distributed to wells of a 96 well microtiter plate at a volume of 100 µl/well. Next, culturing was carried out at 37° C. for 10 to 14 days.

To an ELISA plate coated with 100 ng/ml DROGRP(31-98) was added 100 µl of the above-obtained culture supernatant, which was reacted for 2 hours. After reaction with peroxidase-labeled anti-mouse immunoglobulin G antibody for 1.5 hours, the reaction mixture was developed with a 33', 55'-tetramethylbenzidine (TMBZ) solution. Absorbance at 450 nm was measured, and clones providing at least 0.3 of the absorbance was taken as positive to obtain hybridoma that produces a desired monoclonal antibody. The hybridoma cells were intraperitoneally inoculated into mice treated with pristan, and monoclonal antibody produced in the ascites was recovered. Alternatively, the hybridoma cells were cultured in vitro in a medium, and monoclonal antibody was obtained from the culture supernatant.

The monoclonal antibody was purified according to a conventional procedure by ammonium sulfate precipitation, dialysis to phosphate buffer and purification by a protein A-linked SEPHARASE column to obtain an IgG fraction.

An affinity of the monoclonal antibody thus prepared to DROGRP(31-98) antigen was determined as follows. The DROGRP(31-98) antigen was immobilized to a microtiter plate to saturation, and to the plate was added 20 µl of a solution containing 0 to 0.3 µg/ml monoclonal antibody to the DROGRP(31-98) prepared by dilution of the monoclonal antibody (10 µg/ml), and allowed to react. The antibody bonded to the immobilized DROGRP(31-98) was measured using an enzyme-labeled anti-mouse IgG.

An amount of the bonded antibody [B] was obtained from the relationship between the values of absorbance measured and amounts of the antibody added, and an amount of free antibody (F) was obtained by subtracting an amount of the bonded antibody from an amount of the antibody added. The amount of the bonded antibody [B] was converted to a molar concentration assuming molecular weight of the antibody being 150,000 daltons, and to the obtained molar concentrations the values of B/F were Scatchard-platted. An association constant $Ka=3 \times 10^9 \sim 2 \times 10^{10}$/M was obtained from the slope of Scatchard plotting. From this value the dissociation constant $Kd=3 \times 10^{-8} \sim 5 \times 10^{-7}$M was obtained using the equation $Kd \approx 1/Ka$.

Example 4

Figure 3:
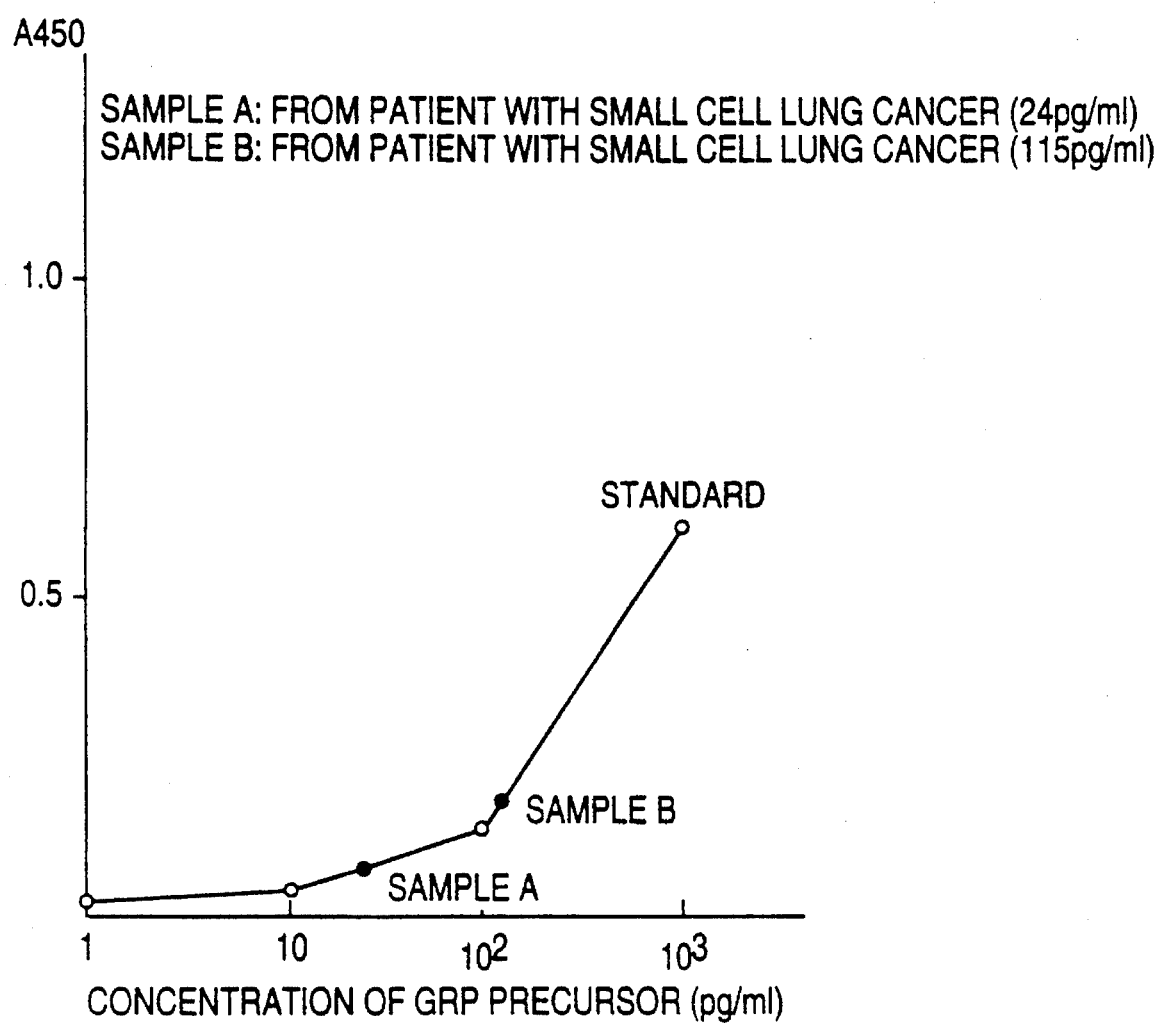

Assay of blood GRP (FIG. 3)

An ELISA plate was coated with 25 µg/ml monoclonal antibody to DROGRP(31-98) according to a conventional procedure, and after adding thereon 200 µl of DROGRP(31-98) standards or 200 µl of sera from patients with small cell lung cancer, 200 µl of peroxidase-labeled polyclonal antibody to DROGRP(31-98) was added to allow reaction. After washing the ELISA plate, a TMBZ solution was added thereon to develop the color, absorbance at 450 nm was measured to prepare a calibration curve, and a concentration of GRP precursor in the blood was obtained using the calibration curve.

Example 5

Figure 4A:
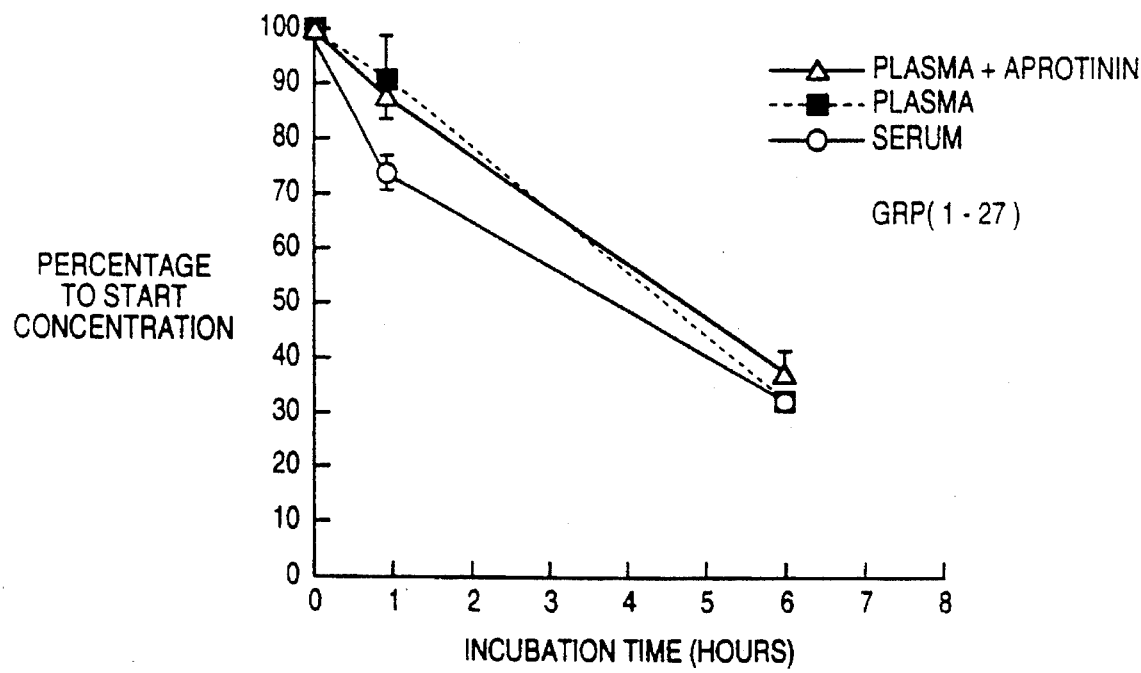
FIGS. 4A and 4B are graphs proGRP showing that (31-98) is more stable than GRP 1-27 in serum or plasma.
Figure 4B:
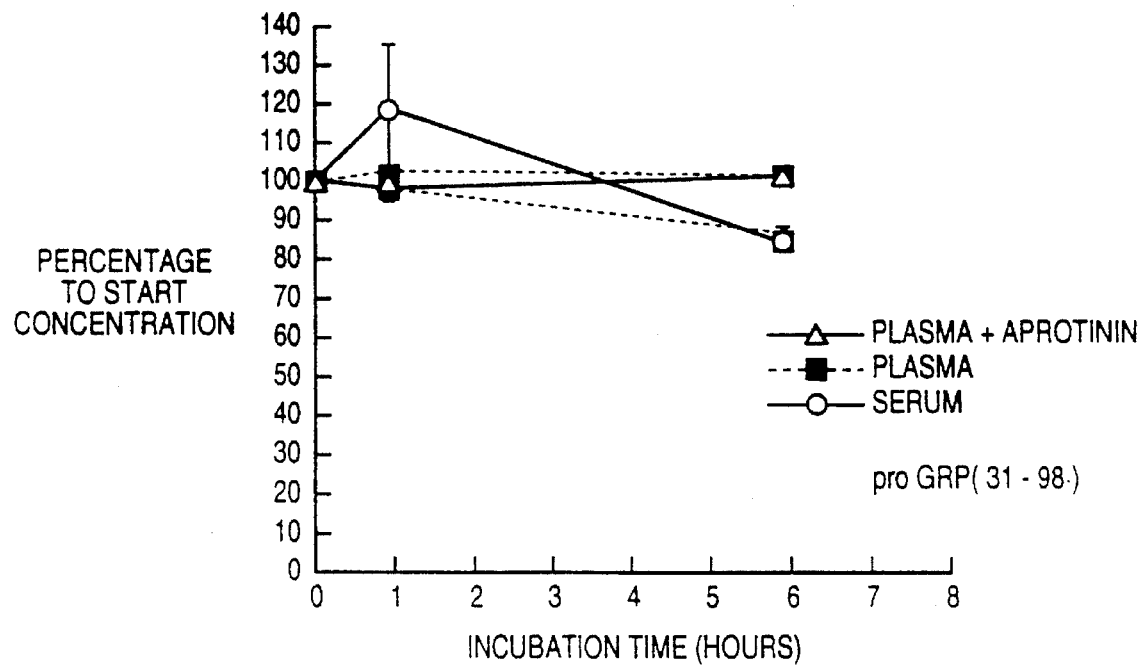

Comparison of stability of GRPs in the blood (FIGS. 4A and 4B)

Stabilities in the blood of GRP(1-27) and DROGRP(31-98) were compared using antibodies to the above-prepared DROGRP(31-98) and antibodies to the conventional GRP(1-27)

A small amount of GRP(1-27) or DROGRP(31-98) was added to a serum, plasma, or aprotinin—containing plasma, and residual concentration of GRP(1-27) and DROGRP(31-98) were determined at 0, 1, and 6 hours from the addition, and percentages of the residual concentration were obtained taking the concentration at the starting point (0 hour) as 100%. As seen from FIG. 4, although the active peptide GRP(1-27) was degraded and disappeared in the presence of serum or plasma, the peptide DROGRP(31-98) was stable for a long time in the serum or plasma.

Example 6

Preparation of monoclonal antibody

The GRP(31-98) prepared as described above was conjugated to a carrier protein, thyroglobulin, the conjugate was dissolved in phosphate buffer (pH 7.4)(PBS(−)) to a concentration of 1.0 mg/ml, and the solution was mixed with a same volume of Freund's complete adjuvant to form a suspension. An amount of the suspension thus prepared containing 0.01 to 0.05 mg of GRP(31-98) was intraperitoneally administered to a BALB/C mouse of 4 to 6 weeks old. After about 12 weeks, the immunized animal was administered with the same concentration of GRP(31-98) solution in PBS(−1) containing about 0.01 to 0.03 mg of DROGRP(31-98) through a tail venous. After 3 days from the administration, the spleen was aseptically removed from the immunized animal.

Next, the spleen was disrupted to single cells by a mesh, and the cells were washed three-times with RPMI-1640 medium. Mouse myeloma cells p3×63 Ag 8 (Nature, 256, 495–497, 1975) in the logarithmic growth phase were cultured for a few days in the presence of 8-azaguanine to completely eliminate reverse mutant, and washed as described above. $1.1 \times 10^7$ cells of the mouse myeloma cell line and $1.4 \times 10^8$ spleen cells prepared as described above were mixed. After centrifugation at 200_×g for 5 minutes, the supernatant was replaced with 1 ml of RPMI-1640 medium containing 50% PEG 4000 (Merck) warmed at 37° C. for cell fusion.

The cells subjected to the cell fusion were centrifuged to remove PEG, and cultured in RPMI-1640 medium containing hypoxanthine, aminopurine and thymidine (abbreviated as HAT hereinafter) as well as 15% fetal calf serum (FCS) for 1 to 2 weeks to allow for hybridomas exclusively to grow. Next, the hybridoma cells were grown in a HAT-free medium for about two weeks, and clones were screened by ELISA as described below to obtain hybridoma producing a monoclonal antibody of the present invention showing a desired reaction specificity. The ELISA was carried out as follows. DROGRP(31-98) was dissolved in phosphate buffer (pH 7.4)(PBS) to a concentration of 1 μg/ml, and 50 μl each of the solution was distributed to each well of a 96-well microtiter plate, and the plate was incubated overnight at 4° C. or for one hour at room temperature for adsorption. After the adsorption, the wells were washed three-times with 0.05% TWEEN 20-containing PBS(–) (abbreviated as T-PBS), and 200 μl/well of 1% BSA-containing PBS(–) was distributed and the plate was incubated at room temperature for one hour. The 1% BSA-containing PBS(–) was removed, and 50 μl/well of hybridoma culture supernatant, crude monoclonal antibody or purified monoclonal antibody was added, followed by reaction for one hour at room temperature. After the reaction, wells were washed three-times with T-PBS, and 50 μl/well of an enzyme-labeled mouse IgG+M antibody (Jackson) diluted 5000-fold with PBS(–) containing 1% BSA, 1% polyvinylpyrrolidone and 0.05% TWEEN20 was added, and reaction was carried out at room temperature for 30 minutes. Non-reacted antibody was eliminated by 4 washings with T-PBS, and 50 μl/well of orthophenylenediamine (OPD) solution (Wako Pure Chemicals) was added for reaction. After 20 minutes of incubation at room temperature, the reaction was terminated with 2N sulfulic acid, and absorbance at 492 nm was measured.

The hybridoma thus obtained were designated as pro-GRP-1E2, proGRP-2B10, proGRP-20D2, pro-GRP-3H1, proGRP-3G2 and proGRP-4C9, and among them the hybridoma proGRP-2B10 and proGRP-3G2 were deposited with Fermentation Research Institute, Agency of Industrial Science and Technology (FRI) under the Budapest Treaty on Dec. 9, 1992 as FERM BP-4110 and FERM BP-4109 respectively. Moreover, the hybridoma proGRP-20D2 was designated as anti-proGRP monoclonal antibody-producing hybridoma (20D2) and was deposited with FRI under the Budapest Treaty on Feb. 10, 1993 as FERM BP-4184.

According to double immunodiffusion using rabbit anti-mouse Ig isotype antibodies (Zymed), isotype of monoclonal antibodies produced by the above-mentioned hybridoma was determined as follows. The monoclonal antibodies GRP-1E2, GRP-2B10 and GRP-3G2 produced by the hybridoma proGRP-1E2, proGRP-2B10 and proGRP-3G2 respectively were IgG1; the monoclonal antibody GRP-20D2 produced by the hybridoma proGRP-20D2 was IgG2; and the monoclonal antibody GRP-3H1 produced by the hybridoma proGRP-3H1 was IgM.

Example 7

ELISA using monoclonal antibodies

The hybridoma proGRP-2B10, proGRP-1E2, proGRP-20D2, proGRP-3H1 and proGRP-409 were intraperitoneally inoculated in mice, and from the ascites, corresponding monoclonal antibodies GRP-2B10, GRP-1E2, GRP-20D2, GRP-3H1 and GRP-409 with at least 90% purity were obtained using a Protein-A column, gel-filtration column or Protein-G column.

ELISA was carried out as follows. GRP(31-98) was dissolved in phosphate buffer (pH 7.4) (PBS) to a concentration of 1 μg/ml, and 50 μl each of the solution was distributed to each well of a 96-well microplate, and the plate was incubated overnight at 4° C. or for one hour at room temperature for adsorption. After the adsorption, the wells were washed three-times with 0.05% TWEEN 20-containing PBS(–) (abbreviated as T-PBS), and 200 μl/well of 1% BSA-containing PBS(–) was distributed and the plate was incubated at room temperature for one hour. The 1% BSA-containing PBS(–) was removed, and 50 μl/well of hydridoma culture supernatant, crude monoclonal antibody or purified monoclonal antibody was added, followed by reaction for one hour at room temperature. After the reaction, wells were washed tree-times with T-PBS, and 50 μl/well of an enzyme-labeled mouse IgG+M antibody (Jackson) diluted 5000-fold with PBS(–) containing 1% BSA, 1% polyvinylpyrrolidone and 0.05% TWEEN 20 was added, and reaction was carried out at room temperature for 30 minutes. Non-reacted antibody was eliminated by 4 washings with T-PBS, and 50 μl/well of orthophenylenediamine (OPD) solution (Wako Pure Chemicals) was added for reaction. After 20 minutes of incubation at a room temperature, the reaction was terminated with 2N sulfuric acid, and absorbance at 492 nm was measured. The result is shown in FIG. 5. As seen from FIG. 5, monoclonal antibody most highly reactive with proGRP (GRP precursor) is GRP-3G2, followed by GRP-2B10, GRP-1E2, GRP-20D2, GRP-3H1 and GRP-4C9 in this order.

Example 8

Production polyclonal antibody

The polypeptide proGRP(31-98) prepared as described above was conjugated to a carrier protein, thyroglobulin, the conjugate was dissolved in phosphate buffer (pH 7.4) (PBS(–)) to a concentration of 1.0 mg/ml, and the solution was mixed with a same volume of Freund's complete adjuvant to form a suspension. An amount of the suspension thus obtained containing 0.1 mg of GRP(31-98) was subcutaneously administered to 1.5–2.0 kg weight rabbit Kb1:JW of 8 weeks old, followed by 6 repeated administrations of 0.07 mg of proGRP(31-98) with ten days intervals. The blood from rabbits which provided a high titer was obtained to prepare polyclonal antibody.

a sandwich ELISA was accomplished using a rabbit anti-proGRP polyclonal antibody as well as the above-mentioned monoclonal antibodies GRP-3G3 and GRP-2B10, as follow.

The monoclonal antibodies GRP-3G2 and GRP-2B10 were diluted with PBS to concentrations of 7 μ/ml and 7 μg/ml respectively (total 14 μg/ml) to form a solution, 100 μl of the diluted monoclonal antibody solution was added to each well to coat the wells at 4° C. overnight. The wells were washed twice with PBS, after addition of 350 μl of 0.5% casein/PBS to wells, incubated at room temperature for 2 hours, and washed twice with PBS. 50 μl/well of a sample-diluting solution (0.1m phosphate buffer pH 7.1, containing 1% BSA, 1% PVP, 0.05% casein, 0.05% TWEEN 20, 10 mM EDTA, and 0.5M NaCl) was added, 50 μl of a sample was added, and after reaction at 37° C. for 2 hours, the wells were washed 5-times with PBS containing 0.05% TWEEN 20.

Figure 6:
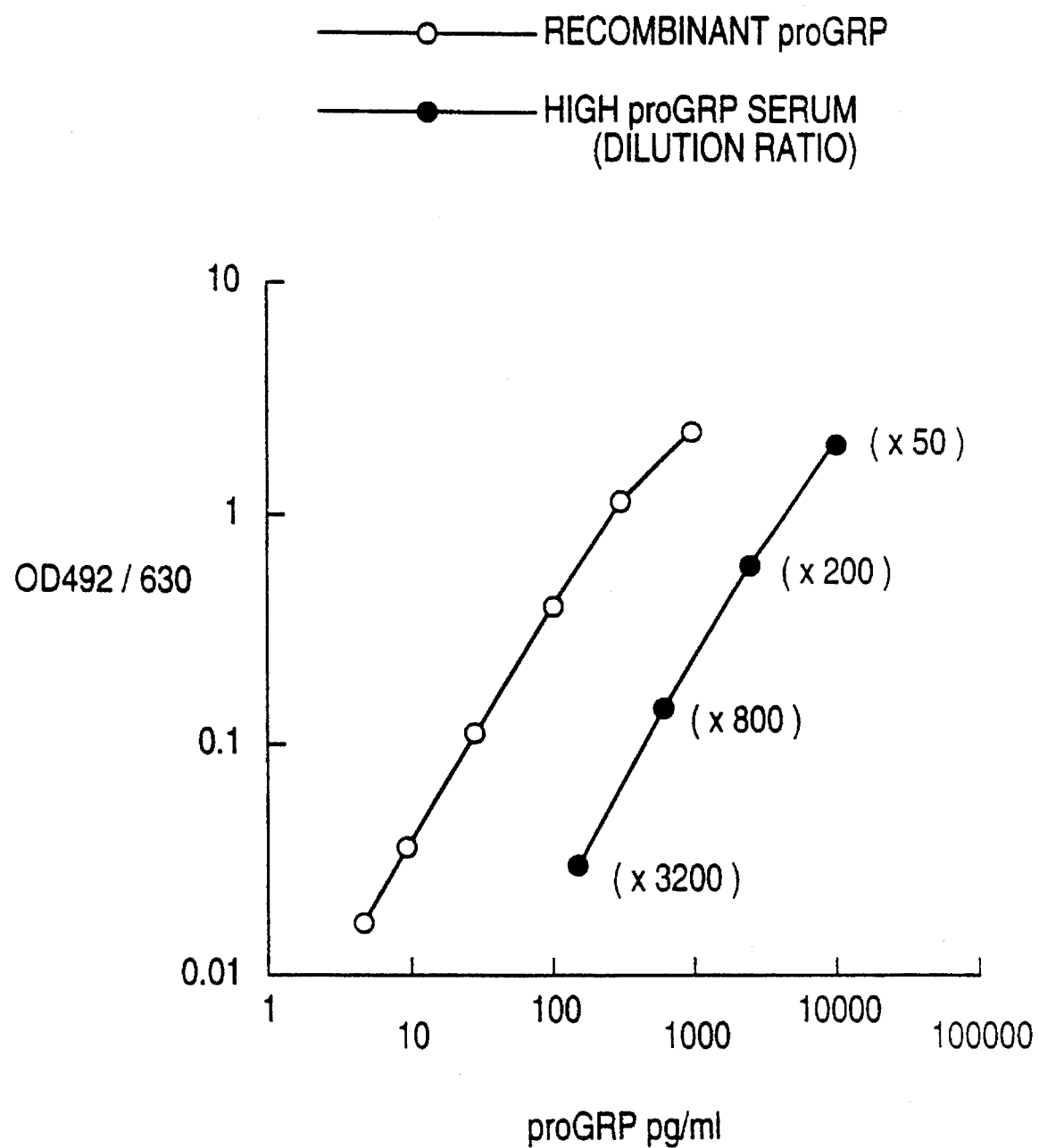
FIG. 6 represents an example of calibration curve for ELISA using the present monoclonal antibodies 3G2 and 2B10 in a mixture as first antibodies and rabbit anti-proGRP polyclonal antibody as second antibody.

Next, 100 μl/well of peroxidase-labeled rabbit anti-proGRP antibody diluted to 5 μg/ml with a labeled antibody diluting solution was added and an incubation was carried out at room temperature for one hour. Next, the wells were washed 5-times with 0.5% TWEEN 20/PBS, 100 μl/well of a substrate solution (orthophenylene diamine (OPD) solution) was added, and after a reaction at room temperature for 30 minutes, the reaction was terminated with 100 μl/well of 2N sulfuric acid. A result obtained by varying concentrations of proGRP(31-98) is shown in FIG. 6. It it considered that the detection limit is about 3 pg/ml, and the measuring range is 10 to 800 pg/ml In addition, result obtained by using samples prepared by diluting a serum of a patient considered to have a high proGRP value with a serum of a normal person at different dilution ratios is shown in FIG. 6. Since a line obtained in the former experiment using a recombinant proGRP(31-98) and a line obtained in the latter experiment using proGRP-containing serum are approximately parallel, it is believed that the reactivity of recombinant proGRP(31-98) with antibodies is similar to the reactivity of a serum proGRP with antibodies.

Next, 7 sera from healthy subjects and 5 sera from patients with small cell lung cancer were tested, and the results are shown in the following table.

| | proGRP value in serum | | |
|---|---|---|---|
| Healthy subjects | proGRP pg/ml | Patient with small cell lung cancer | proGRP pg/ml |
| No. 1 | 20.0 | No. 1 | 18,300 |
| No. 2 | 39.0 | No. 2 | 21,300 |
| No. 3 | 5.7 | No. 3 | 352 |
| No. 4 | 7.4 | No. 4 | 143 |
| No. 5 | 3.8 | No. 5 | 3,200 |
| No. 6 | 8.7 | | |
| No. 7 | 24.5 | | |

As seen from the above results, the highest value of proGRP of healthy subjects is 39 pg/ml, while the values of proGRP of patients with small cell lung cancer are at least 143 pg/ml, the highest value in the patients is 21,300 pg/ml. There is a big difference between proGRP value in serum from a healthy subject and that from a patient with small cell lung cancer, demonstrating that proGRP is highly useful as a marker for diagnosing small cell lung cancer.

In summary, since the present antibody to an inactive region in GRP precursor, i.e., proGRP(31-98) has a high affinity to GRP precursor and GRP precursor is highly stable in the blood in comparison with active GRP, then lung cancer, especially small cell lung cancer, can be diagnosed with high reliability by detecting or measuring GRP precursor in the blood using the present antibodies.

We claim:

1. A monoclonal antibody having an association constant $K_a$ of $3\times10^9$–$2\times10^{10}$/M obtained from a hybridoma cell line selected from the group consisting of proGRP-2B10 (FERM BP-4110), proGRP-3G2 (FERM BP-4109), and proGRP-2OD2 (FERM BP-4184).

2. A hybridoma cell line selected from the group consisting of proGRP-2B10 (FERM BP-4110), proGRP-3G2 (FERM BP-4109), and proGRP-2OD2 (FERM BP-4184).

3. A diagnostic agent for lung cancer comprising a monoclonal antibody according to claim 1 and a carrier.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 204 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..204

( x i ) SEQUENCE DESCRIPTION: SEQ ID NO:1:

```
AGT  ACT  GGT  GAG  AGC  TCT  TCT  GTT  TCT  GAA  CGT  GGA  TCC  CTT  AAG  CAG      48
Ser  Thr  Gly  Glu  Ser  Ser  Ser  Val  Ser  Glu  Arg  Gly  Ser  Leu  Lys  Gln
 1                  5                        10                       15

CAG  CTT  CGC  GAA  TAC  ATC  CGT  TGG  GAA  GAA  GCT  GCT  CGT  AAC  CTG  CTA      96
Gln  Leu  Arg  Glu  Tyr  Ile  Arg  Trp  Glu  Glu  Ala  Ala  Arg  Asn  Leu  Leu
               20                       25                       30

GGC  CTG  ATC  GAA  GCT  AAA  GAA  AAC  CGT  AAC  CAC  CAG  CCG  CCG  CAG  CCG     144
Gly  Leu  Ile  Glu  Ala  Lys  Glu  Asn  Arg  Asn  His  Gln  Pro  Pro  Gln  Pro
          35                        40                        45

AAA  GCT  TTA  GGT  AAC  CAG  CAG  CCG  TCT  TGG  GAC  TCT  GAA  GAC  TCT  TCG     192
Lys  Ala  Leu  Gly  Asn  Gln  Gln  Pro  Ser  Trp  Asp  Ser  Glu  Asp  Ser  Ser
     50                        55                        60

AAC  TTT  AAA  GAC                                                                  204
Asn  Phe  Lys  Asp
 65
```

( 2 ) INFORMATION FOR SEQ ID NO:2:

( i ) SEQUENCE CHARACTERISTICS:
        ( A ) LENGTH: 68 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Ser | Thr | Gly | Glu | Ser | Ser | Ser | Val | Ser | Glu | Arg | Gly | Ser | Leu | Lys | Gln |
| 1 | | | | 5 | | | | | 10 | | | | | 15 | |

| Gln | Leu | Arg | Glu | Tyr | Ile | Arg | Trp | Glu | Ala | Ala | Arg | Asn | Leu | Leu |
| | | | 20 | | | | | 25 | | | | 30 | | |

| Gly | Leu | Ile | Glu | Ala | Lys | Glu | Asn | Arg | Asn | His | Gln | Pro | Pro | Gln | Pro |
| | | | 35 | | | | 40 | | | | | 45 | | | |

| Lys | Ala | Leu | Gly | Asn | Gln | Gln | Pro | Ser | Trp | Asp | Ser | Glu | Asp | Ser | Ser |
| | 50 | | | | | 55 | | | | | 60 | | | | |

Asn Phe Lys Asp
65

( 2 ) INFORMATION FOR SEQ ID NO:3:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

AATTCATGAG TACTGGTGAG AGCTCTTCTG TTTCTGAACG TGGATCC     47

( 2 ) INFORMATION FOR SEQ ID NO:4:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CTTAAGCAGC AGCTTCGCGA ATACATCCGT TGGGAAGAAG CTGCTCGTAA CCTG     54

( 2 ) INFORMATION FOR SEQ ID NO:5:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CTAGGCCTGA TCGAAGCTAA AGAAAACCGT AACCACCAGC CGCCGCAGCC GAAA     54

( 2 ) INFORMATION FOR SEQ ID NO:6:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GCTTTAGGTA ACCAGCAGCC GTCTTGGGAC TCTGAAGACT CTTCGAACTT TAAAGACTAA     60

TAAG     64

( 2 ) INFORMATION FOR SEQ ID NO:7:

( i ) SEQUENCE CHARACTERISTICS:
　　　　( A ) LENGTH: 49 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:7:

CTTAAGGGAT CCACGTTCAG AAACAGAAGA GCTCTCACCA GTACTCATG    49

( 2 ) INFORMATION FOR SEQ ID NO:8:

( i ) SEQUENCE CHARACTERISTICS:
　　　　( A ) LENGTH: 54 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:8:

GCCTAGCAGG TTACGAGCAG CTTCTTCCCA ACGGATGTAT TCGCGAAGCT GCTG    54

( 2 ) INFORMATION FOR SEQ ID NO:9:

( i ) SEQUENCE CHARACTERISTICS:
　　　　( A ) LENGTH: 54 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:9:

TAAAGCTTTC GGCTGCGGCG GCTGGTGGTT ACGGTTTTCT TTAGCTTCGA TCAG    54

( 2 ) INFORMATION FOR SEQ ID NO:10:

( i ) SEQUENCE CHARACTERISTICS:
　　　　( A ) LENGTH: 62 base pairs
　　　　( B ) TYPE: nucleic acid
　　　　( C ) STRANDEDNESS: single
　　　　( D ) TOPOLOGY: linear (ii) MOLECULE TYPE: DNA (genomic)

( x i ) SEQUENCE DESCRIPTION: SEQ ID NO:10:

TCGACTTATT AGTCTTTAAA GTTCGAAGAG TCTTCAGAGT CCCAAGACGG CTGCTGGTTA    60
CC    62